United States Patent [19]
Jamison

[11] 4,368,429
[45] Jan. 11, 1983

[54] METHOD AND APPARATUS FOR SUPPRESSING NOISE DURING NONDESTRUCTIVE EDDY CURRENT TESTING

[75] Inventor: Thomas D. Jamison, Fort Oglethorpe, Ga.

[73] Assignee: Combustion Engineering, Inc., Windsor, Conn.

[21] Appl. No.: 149,828

[22] Filed: May 15, 1980

[51] Int. Cl.³ .................. G01N 27/90; G01R 33/12; H04B 15/00
[52] U.S. Cl. ................................ 324/225; 307/520; 324/220; 324/233; 328/165
[58] Field of Search ............. 324/233, 234, 236, 237, 324/225; 328/165, 167; 455/303, 305, 306; 307/520, 521

[56] References Cited

U.S. PATENT DOCUMENTS

| 3,375,451 | 3/1968 | Borelli et al. | 328/165 X |
| 3,526,842 | 9/1970 | Andrew | 328/165 |
| 3,961,172 | 6/1976 | Hutcheon | 328/167 X |
| 4,004,239 | 1/1977 | Clarke | 328/167 X |
| 4,027,264 | 5/1977 | Gutleber | 328/167 |
| 4,037,095 | 7/1977 | Howells et al. | 328/165 X |
| 4,061,968 | 12/1977 | Pigeon | 324/234 |
| 4,215,310 | 7/1980 | Schwerer | 324/225 |
| 4,274,054 | 6/1981 | Savidge et al. | 324/237 |

Primary Examiner—Gerard R. Strecker
Attorney, Agent, or Firm—William W. Habelt

[57] ABSTRACT

A filter apparatus (2) is disclosed for filtering out any reoccurring noise (5) present in a defect signal (1) received from a flaw detection device (4) such as an eddy current test probe. Filter circuit means (10) receives the defect signal generated by the flaw detector device and produces an output signal (5) duplicative of any reoccurring noise present therein. A differential amplifier (50) subtracts the output signal (5) of the filter circuit means from the defect signal (1) generated by the flaw detection device and amplifies the difference. A filtered defect signal (9) void of any reoccurring noise is thereby produced.

6 Claims, 5 Drawing Figures 4,368,429

METHOD AND APPARATUS FOR SUPPRESSING NOISE DURING NONDESTRUCTIVE EDDY CURRENT TESTING

BACKGROUND OF THE INVENTION

The present invention relates to nondestructive eddy current testing of metallic workpieces, and more particularly, to a method and apparatus for filtering from the defect signal any reoccuring noise present therein.

In the art of nondestructive testing, the use of eddy current techniques and equipment is well known. More specifically, eddy current means have been used to detect various defects in tubular members, such as cracks, inclusions, thinning and the like. In the typical nondestructive test of tubular member using eddy current techniques, an eddy current probe is passed through the tubular member to detect any defects in the wall of the tubular member. The eddy current probe includes sensing means for detecting the defect and for generating a defect signal representative of the defect and informative of the various characteristics of the defect such as depth, size and location.

One particular application of nondestructive eddy current testing is the inspection of the typically long and coiled heat exchange tubes of steam generators and process heaters. One problem frequently encountered when inspecting such heat exchange tubes is the presence of noise in the defect signal from the eddy current probe sensing means which can frequently mask smaller defects which, if undetected can lead to potential catastrophic failures at a later date. Much of the noise is generated from anomalies in the inner surface of the tube resulting from manufacturing operations such as plug chatter, reeling marks, pilgering and the like. Additionally, if the heat exchange tubes are finned on their outer surface, a noise signal is generated by the presence of the fins. In order to avoid problems with repetitive noise in the tubes, manufacturers have gone through elaborate manufacturing operations to ensure such anomalies are not present in their product and have been forced to eliminate fins on applications where inspection is necessary.

One known technique for handling the noise generated by such tube anomalies is termed multicurrent or multifrequency eddy current testing. In this known technique, a second current or frequency is utilized to generate a second defect signal having a different frequency than the first defect signal. The two signals are then processed in a manner such as disclosed in U.S. Pat. No. 4,061,968 through elimination circuits to remove the undesirable noise.

However, such multifrequency, eddy current testing is by its very nature more difficult, time consuming and expensive than single frequency eddy current testing. Therefore, it is an object of this invention to provide a single frequency eddy current apparatus which is capable of filtering any reoccurring noise out of the defect signal.

SUMMARY OF THE INVENTION

The present invention provides an improved apparatus for inspecting a tubular member wherein any reoccurring noise present in the defect signal is filtered therefrom. The improvement comprises equipping a typical single frequency eddy current probe with filter circuit means for receiving the signal generated by the eddy current probe sensing means and producing as an output signal duplicative of any reoccuring noise present in the received signal, and a differential amplifier for subtracting the noise signal generated in the filter circuit from the signal generated by the eddy current probe sensing means and amplifying the difference therebetween. Thus, a filtered output signal representative of the defect is produced.

In one embodiment of the invention, the filter circuit means incorporates a phase-locked loop for receiving the signal generated by the eddy current probe sensing means and producing as its output a signal synchronized in phase and frequency with the reoccurring noise present in the defect signal. A gain controlled amplifier is provided for receiving the output signal of the phase-locked loop and for producing at its output an amplified reproduction of the output signal of the phase-locked loop. The gain of the amplifier is varied in response to an error voltage produced by a comparator which compares the synchronous output signal of the phase-locked loop to the defect signal generated by the eddy current probe sensing means. This error voltage is indicative of the amplitude differential between the synchronous output signal of the phase-locked loop and the defect signal generated by the eddy current probe sensing means.

DETAILED DESCRIPTION OF THE PREFERRED EMBODIMENT

Figure 1:
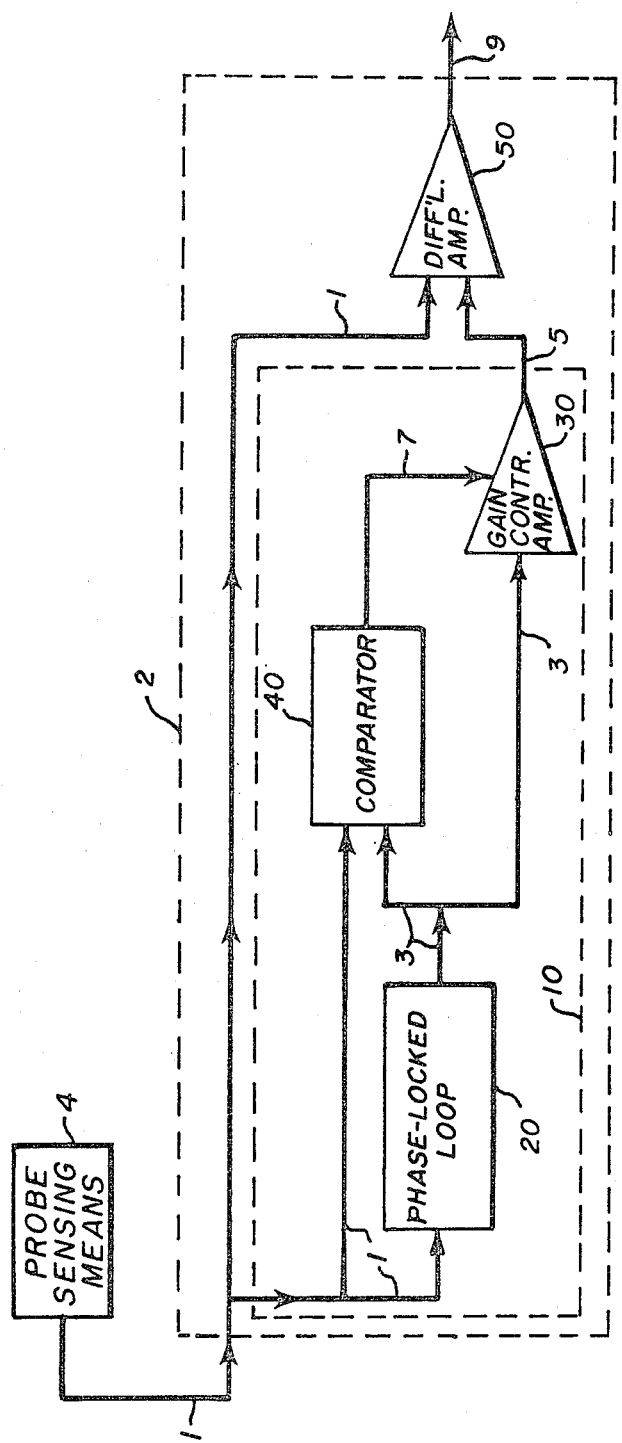
FIG. 1 is a block diagram of a filter apparatus according to the present invention.
Figure 2:
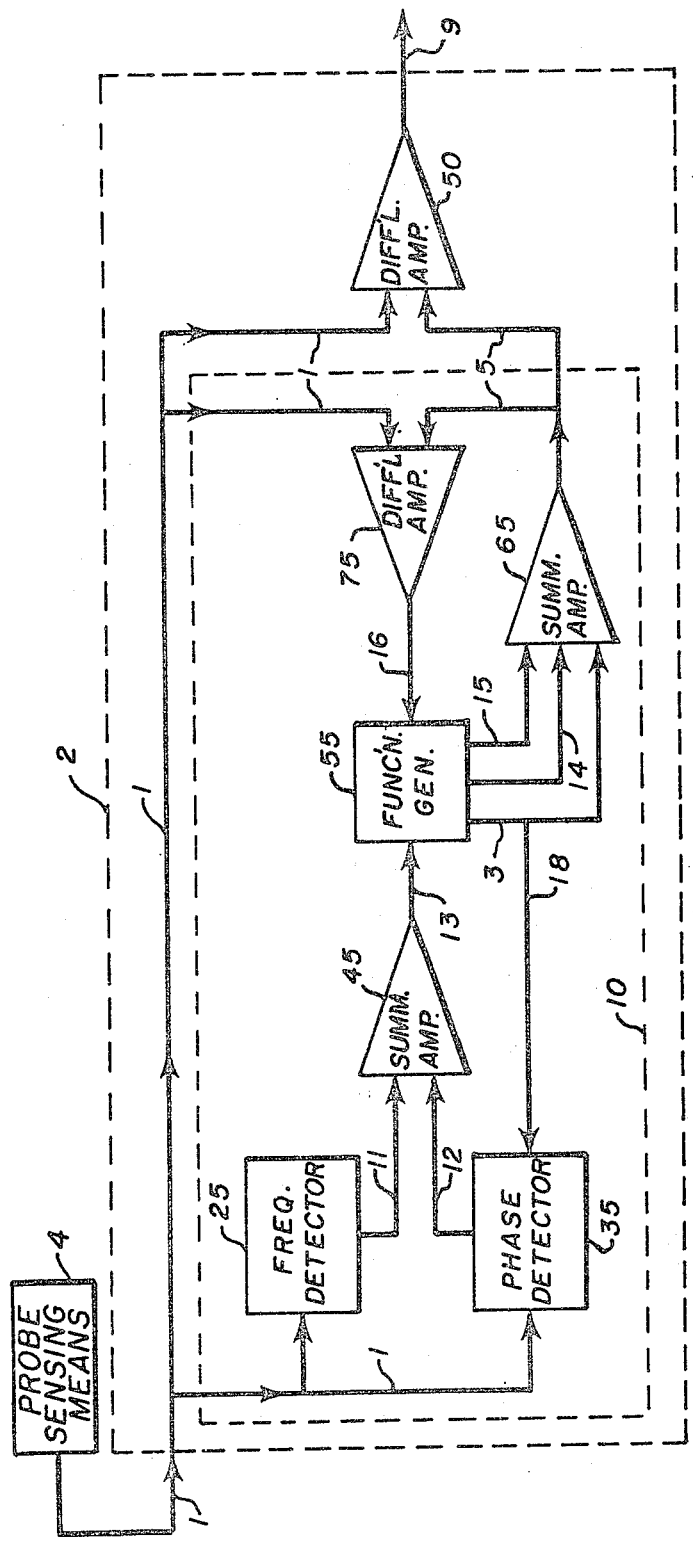
FIG. 2 is a block diagram depicting an alternate embodiment of a filter apparatus according to the present invention.

Referring now to the drawing, and more particularly to FIGS. 1 and 2 thereof, there is depicted in block diagram form alternate embodiments of a filter apparatus 2 designed in accordance with the present invention. The incoming defect signal 1 generated by the eddy current probe sensing means 4 is received by the filter apparatus 2 and processed therein to remove any reoccurring, i.e., repetitive, noise present in the incoming defect signal 1 thereby producing as the output of the filter apparatus 2 a filtered defect signal 9.

In accordance with the present invention, the filter apparatus 2 comprises filter circuit means 10 for receiving the defect signal 1 generated by the eddy current probe sensing means 4 and for producing as its output a noise signal 5 duplicative of any reoccurring noise present in the incoming defect signal 1, and a differential amplifier 50 for subtracting the noise signal 5 generated in the filter circuit means from the incoming defect signal 1 and amplifying the difference therebetween. The noise signal 5 produced in filter circuit means 10 has the same frequency, phase and amplitude as the reoccurring noise present in the incoming defect signal 1. By subtracting the noise signal 5 from the incoming defect signal 1, the filtered defect signal 9 is obtained.

In the embodiment of the present invention shown in FIG. 1, the filter circuit means 10 comprises a phase-locked loop 20, a gain controlled amplifier 30 and a comparator 40. The phase-locked loop 20 is a versatile feedback system, well known in the art, that provides frequency selective filtering without the use of inductors. A phase-locked loop contains three basic functional elements: a phase comparator, a voltage controlled oscillator and a low pass filter. A phase-locked loop is generally packaged as an integrated circuit. The phase comparator compares the phase and frequency of input signal 1 to the phase and frequency of the signal generated by the voltage controlled oscillator and produces an error voltage proportional to the phase and frequency difference therebetween. The error voltage is filtered by the low pass filter; the filtered signal is the input to the voltage controlled oscillator. The voltage controlled oscillator output is output noise signal 3 of phase-locked loop 20. The voltage controlled oscillator output frequency varies proportionally to the varying magnitude of the error signal.

With no input signal 1 to the phase-locked loop 20, the voltage controlled oscillator operates at a center frequency predetermined as the "free-running" frequency as determined generally by a resistor and capacitor external to the integrated circuit. With an input signal 1 to the phase-locked loop 20, if the frequency of input signal 1 is sufficiently close to the frequency of the signal generated by the voltage controlled oscillator, the error signal feeds back to cause the voltage controlled oscillator to change frequency until the error signal is reduced to zero, in turn the voltage controlled oscillator synchronizes or is said to "lock" with the frequency of the incoming signal 1. Thus, phase-locked loop 20 produces noise signal 3 which is synchronized in phase and frequency with any re-occuring noise present in the incoming defect signal 1.

The band of frequencies in the vicinity of the free-running frequency where the phase-locked loop can establish or acquire lock with incoming defect signal 1 is the "capture range" or "acquisition range". The capture range is related to the low pass filter bandwidth and decreases as the low pass filter bandwidth is reduced.

Once the phase-locked loop has locked onto the frequency of incoming defect signal 1, the frequency of incoming defect signal 1 and hence the locked frequency can go outside the capture range. The band of frequencies in the vicinity of the free-running frequency over which the phase-locked loop can maintain lock with the incoming defect signal 1 is the "lock" range, "tracking" range or "holding" range. The tracking range is a broader band of frequencies than the capture range and increases as the overall loop gain of the phase-locked loop is increased.

Thus, a phase-locked loop responds only to those frequencies in incoming defect signal 1 close to the voltage controlled oscillator free-running frequency within the capturing range and therefore offers a high degree of frequency selectivity with the selectivity characteristics centered about the free-running frequency. The free-running frequency can be established by choice of circuit components external to the integrated circuit.

When the frequency of re-occuring noise in incoming defect signal 1 varies, phase-locked loop 20 will remain locked onto the frequency of the noise as long as the frequency of the noise is within the tracking range of phase-locked loop 20. The output of the voltage controlled oscillator will also remain within the tracking range of frequencies. It is therefore possible to monitor a selective frequency range, the tracking range of phase-locked loop 20, as determined by external circuit components. If a different tracking range is to be monitored, the external circuit elements may be changed accordingly. Phase-locked loop 20 serves as a means for producing a noise signal synchronized in phase and frequency with any reoccurring noise present in the defect signal. Phase-locked loop 20 receives the incoming defect signal 1 at its input terminal and produces at its output terminal a noise signal 3 synchronized in phase and frequency with any reoccurring noise present in the incoming defect signal 1.

The gain controlled amplifier 30 receives at its input port the output noise signal 3 from the phase-locked 20 and produces at its output port an amplified reproduction 5 of the output noise signal 3 of the phase-locked loop 20. The gain of amplifier 30 is varied in response to an error voltage 7, which is indicative of the amplitude differential between the output noise signal 3 of the phase-locked loop 20 and the incoming defect signal 1, such that the magnitude of amplified representation 5 at the output port of gain controlled amplifier 30 is the same magnitude as the magnitude of incoming defect signal 1. Phase-locked loop 20 generates output noise signal 3 with the same phase and frequency as the incoming defect signal 1. A graphical example may be seen by comparing the phase and frequency of incoming defect signal 1 in FIG. 3a with the phase and frequency of output noise signal 3 in FIG. 3b and noting that the phase and frequency are identical.

Gain controlled amplifier 30 adjusts only the magnitude of output noise signal 3 resulting in amplified reduction 5 that has the same phase, frequency and magnitude as the incoming defect signal 1. The effect produced by varying the gain of gain controlled amplifier 30 may be seen by graphical example by comparing the magnitude of output noise signal 3 and the magnitude of amplified reproduction 5 in FIG. 3b to the magnitude of incoming defect signal 1 shown in FIG. 3a and noting that the magnitudes of amplified reproduction 5 and incoming defect signal 1 are identical.

The error voltage 7 is produced in circuit means 40, preferably, a comparator. Comparator 40 has a first input port for receiving the incoming defect signal 1, a second input port for receiving the output noise signal 3 of the phase-locked loop 20 and an output port at which the error voltage 7 is presented. The comparator 40 compares the output noise signal 3 of the phase-locked loop 20 to the incoming defect signal 1 and produces the error voltage 7 as an indication of the amplitude differential between the output noise signal 3 of the phase-locked loop 20 and the incoming defect signal 1.

The differential amplifier 50 receives the incoming defect signal 1 at its first input port and the amplified representation 5 of the output noise signal 3 of the phase-locked loop 20 at its second input port. The differential amplifier 50 then subtracts the amplifier representation 5 from the incoming defect signal 1 and amplifies the difference therebetween, thereby producing a filtered defect signal 9 which is indicative of only a defect present in the wall of the tubular member. A graphical example may be seen in FIGS. 3a, 3b and 3c where the amplified representation 5 of FIG. 3b as subtracted from the incoming defect signal 1 of FIG. 3a results in the defect signal 9 of FIG. 3c.

The embodiment shown in FIG. 1 has particular application in instances where the reoccurring noise present in the defect signal takes the form of a simple sinusoidal wave. In many instances, however, the reoccurring noise present in the defect signal will be a periodic function but will take a form other than a simple sinusoidal wave. In such an instance, the alternate embodiment of the present invention shown in FIG. 2 is preferred.

In the alternate embodiment of the invention shown in FIG. 2, the filter circuit means 10 comprises a frequency detector 25, a phase detector 35, a first summing amplifier 45, a function generator 55, a second summing amplifier 65, and a differential amplifier 75. Phase detector 35, frequency detector 25, and summing amplifier 45 serve a means for producing a voltage signal indicative of the phase and frequency of any reoccurring noise present in the defect signal.

The frequency detector 25 receives the incoming defect signal 1 at its input terminal. Frequency detector 25 is a frequency-to-voltage converter, which is well known in the art. Frequency detector 25 detects the frequency of re-occurring noise present in incoming defect signal 1 and produces as its output a voltage signal 11 that is proportional in magnitude to the frequency of any reoccurring noise present in the incoming defect signal 1. Phase detector 35 receives the incoming defect signal 1 at its first input port and a feedback signal 18, from the function generator 55 at its second input port, the feedback signal 18 being a periodic wave having the same frequency as the incoming defect signal 1. The phase detector 35 then determines what phase shift, α, both in magnitude and sign, exists between the incoming defect signal 1 and the feedback signal 18 and generates as its output a voltage signal 12 as a representation of that phase shift.

Summing amplifier 45 receives both the voltage signal 11 from the frequency detector 25 and the voltage signal 12 from the phase detector 35. Voltage signal 11 is a voltage signal that is proportional in magnitude to the frequency of any re-occuring noise present in the incoming defect signal 1. Voltage signal 11 is the major component of voltage signal 13, the output of summing amplifier 45, the voltage that controls the frequency of the output of function generator 55. The smaller component of voltage signal 13 is voltage signal 12, the output of phase detector 35. Phase detector 35 detects a phase difference indicating the frequency of reoccurring noise in incoming defect signal 1 is changing. The contribution of voltage signal 12 to voltage signal 13 in summing amplifier 45 serves to adjust the frequency of function generator 55 output voltage signal 13 to maintain the frequency of feedback signal 18 the same as the frequency of reoccurring noise in incoming defect signal 1. When the frequency of function generator 55 output voltage signal 13 is the same as the frequency of reoccurring noise in incoming defect signal 1, voltage signal 12 decreases to zero. In this manner, summing amplifier 45 generates as its output a voltage signal 13 whose magnitude is indicative of a periodic function synchronized in phase and frequency with the incoming defect signal 1.

The function generator 55 is a voltage controlled oscillator. The function generator 55 output frequency and phase varies proportionally to the magnitude of voltage signal 13. The function generator 55 output magnitude varies proportionally to the magnitude of feedback error signal 16. The function generates 55 receives at its first input terminal the voltage signal 13 from the summing amplifier 45 and, based on signal 13, generates a periodic sinusoidal noise signal 3 which is synchronized in phase and frequency with the incoming defect signal 1. Simultaneously, the function generator 55 receives a feedback error signal 16 at its second input terminal, this feedback error signal 16 representing the magnitude differential which exists between magnitude of the amplified reproduction 5 of the periodic sinusoidal noise signal 3 and the magnitude of any periodic noise present in the defect signal 1. The function generator 55 then produces as further output in addition to the periodic sinusoidal noise signal 3, a square wave and a saw-tooth function signal 14 and 15. Square wave 14 is produced from periodic sinusoidal noise signal 3 by detecting zero crossings and generating a square wave of the same frequency as periodic sinusoidal noise signal 3. Saw-tooth function signal 14 is produced from square wave 15 by integrating each half-cycle of square wave 14. Saw-tooth function signal 15 is therefore the same frequency as periodic sinusoidal noise signal 3 and square wave 14.

Summing amplifier 65 receives the periodic sinusoidal noise signal 3 and the square wave and saw-tooth signals 14 and 15 from the function generator, sums them and produces an amplified periodic noise signal 5 representative of any reoccurring noise present in the defect signal 1.

The feedback error signal 16 which is input to the function generator 55 is produced by differential amplifier 75. Differential amplifier 75 receives the incoming defect signal 1 at its first input port and the amplified periodic noise signal 5 at its second input port. The differential amplifier 75 then substracts the amplified periodic noise signal 5 from the incoming signal and feeds the differential back to the function generator 55. The differential amplifier 75 is produced with a predetermined amount of lag to ensure that the noise signal 5 is compared to the same incoming defect signal 1 from which it was generated.

The differential amplifier 50 also receives the incoming defect signal 1 at its first input port and the amplified periodic noise signal 5 from the summing amplifier 65 at its second input port. The differential amplifier 50 then subtracts the amplified periodic noise signal 5 from the incoming defect signal 1 and amplifies the difference between, thereby producing a filtered defect signal 9 which is indicative of only a defect present in a metallic workpiece, such as the wall of a tubular member.

Figure 3A:
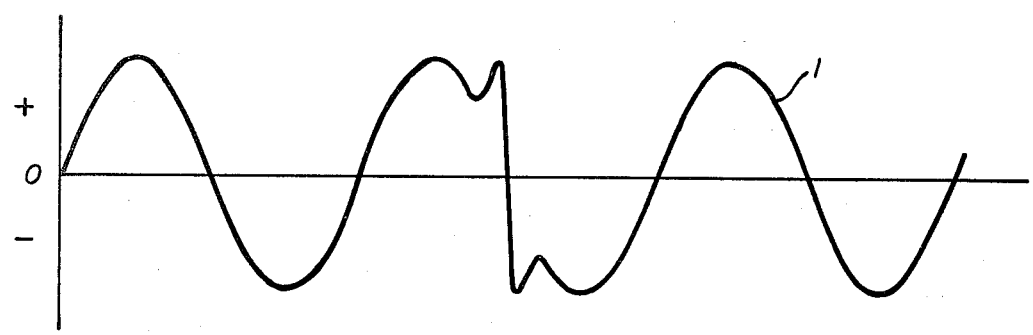
FIGS. 3a, 3b and 3c illustrates oscilloscope traces of the received defect signal, the synchronous noise signal and the filtered defect signal.
Figure 3B:
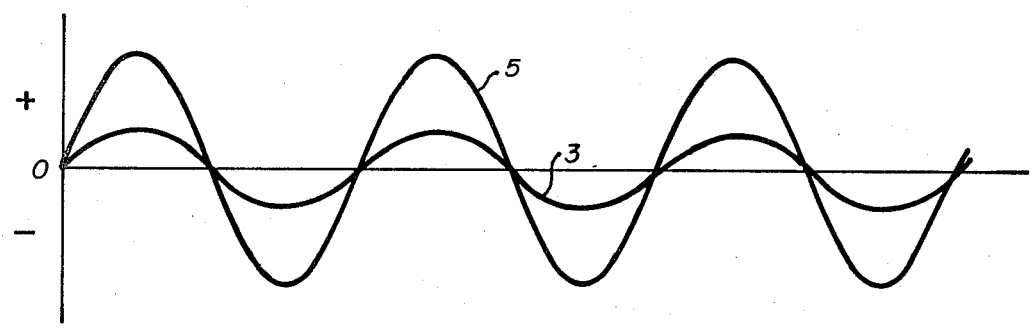
Figure 3C:
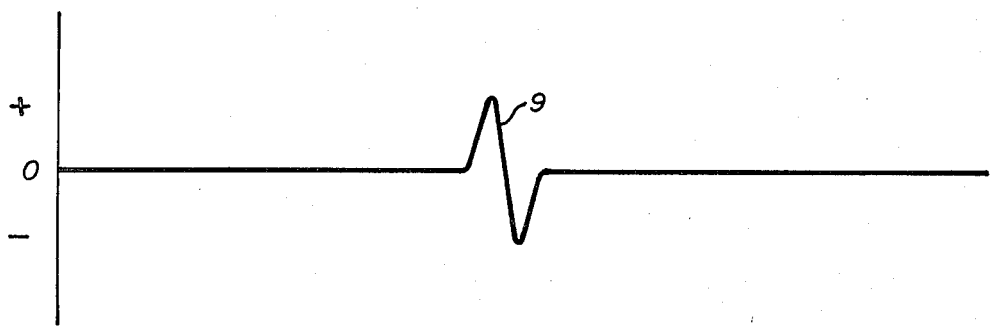

The operation of filter apparatus 2 can best be described with reference to FIGS. 3a, 3b and 3c wherein typical oscilloscope traces of the various signals are illustrated. The incoming defect signal 1 is received by the filter apparatus 2. A duplication 5 of any reoccuring noise within the incoming defect signal 1 is produced by generating a signal synchronized in phase and frequency with any reoccurring noise present in the received defect signal 1 and adjusting the amplitude of the synchronous signal to match the amplitude of the incoming defect signal. The amplified synchronous signal 5 is then subtracted from the incoming defect signal 1 thereby filtering out any reoccurring noise present in the incoming defect signal 1 and producing a filtered defect signal 9 representative of only any defects present in the tube wall and free of any reoccurring anomalies, such as plug chatter, reeling marks or attachments such as fins.

Although the invention has been described in relation to an eddy current probe, the filter apparatus 2 may have many other applications of flaw detection which will be apparent to those skilled in the art in light of the foregoing disclosure. Accordingly, the appended claims are meant to include all such applications, alterations and modifications as fall within their scope.

I claim:

1. An apparatus for inspecting metallic workpieces comprising:
   a. sensing means for detecting a defect in the metallic workpiece and for generating a signal representative of the defect;
   b. a phase-locked loop for receiving the signal generated by said sensing means and for producing as an output a signal synchronized in phase and frequency with said reoccurring noise present in the received signal;
   c. a gain controlled amplifier for receiving the output signal of said phase-locked loop for producing as an output an amplified reproduction of the output signal of said phase-locked loop, the gain of said amplifier being varied in response to an error voltage indicative of the amplitude differential between the output signal of said phase-locked loop and the signal generated by said sensing means;
   d. a comparator for comparing the output signal of said phase-locked loop to the signal generated by said sensing means for producing as an output an error voltage indicative of the amplitude differential between the output signal of said phase-locked loop and the signal generated by said sensing means, said comparator having a first input port for receiving the signal generated by said sensing means, a second input port for receiving the output signal of said phase-locked loop and an output port at which the error voltage is presented; and
   e. a differential amplifier for subtracting the output error voltage signal of said gain controlled amplifier from the signal generated by said sensing means and amplifying the difference therebetween, thereby producing a filtered defect signal, said differential amplifier having a first input port for receiving the signal from said sensing means, a second input port for receiving the output error voltage from said gain controlled amplifier and an output port at which the filtered defect signal is presented.

2. An apparatus for filtering an incoming signal to remove any reoccurring noise present in the incoming signal comprising:
   a. a phase-locked loop for receiving the incoming signal and for producing as an output signal synchronized in phase and frequency with said reoccurring noise, said phase-locked loop having an input port at which the incoming signal is received and an output port at which the output signal of said phase-locked loop is presented;
   b. a gain controlled amplifier having an input port and an output port, receiving at its input port the output signal of said phase-locked loop and for producing as an output an amplified reproduction of the output signal of said phase-locked loop, the gain of said amplifier being varied in response to an error voltage indicative of the amplitude differential between the output signal of said phase-locked loop and the incoming signal;
   c. a comparator for comparing the output signal of said phase-locked loop to the incoming signal and for producing as an output an error voltage indicative of the amplitude differential between the output signal of said phase-locked loop and the incoming signal, said comparator having a first input port for receiving the output signal of said phase-locked loop, a second input port for receiving the incoming signal and an output port at which the error voltage is presented, and
   d. a differential amplifier for subtracting the output error voltage signal of said gain controlled amplifier from the incoming signal and for producing as an output an amplification of the difference therebetween, said differential amplifier having a first input port for receiving the incoming signal, a second input port for receiving the output error voltage signal from said gain controlled amplifier and an output port at which the amplification of the difference between the incoming signal and the output error voltage signal is presented.

3. An apparatus for inspecting metallic work pieces comprising:
   a. sensing means for detecting a defect in the metallic workpiece and for generating a signal representative of the defect;
   b. circuit means for receiving the signal generated by said sensing means and for producing a voltage signal indicative of the frequency and phase of any reoccurring noise present in the received signal;
   c. a function generator for producing as its output a primary function signal synchronized in phase and frequency with said reoccurring noise present in the signal generated by said sensing means, said primary function being a periodic sinusoidal wave, a first secondary function signal, said first secondary function signal being a square wave function, and a second secondary function signal, said second secondary function signal being a saw-tooth wave function, said function generator having a first input port for receiving a voltage signal indicative of the frequency and phase of said reoccurring noise, and a second input port for receiving a feedback error signal representing the differential existing between the noise signal produced by said function generator and the signal generated by said sensing means;
   d. a summing amplifier having a first input port for receiving the primary function signal produced by said function generator, a second input port for receiving the first secondary function signal produced by said function generator, a third input port for receiving the second secondary function signal produced by said function generator, and an output port, said summing amplifier producing as an output a noise signal duplicative of any reoccurring noise present in the signal generated by said sensing means, said noise signal being an amplified summation of the primary function signal, the first secondary function signal, and the second secondary function signal produced by said function generator;
   e. a first differential amplifier for substracting the noise signal produced in said summing amplifier from the signal generated by said sensing means, and for producing as an output signal an amplified reproduction of the differential therebetween, said output signal being the feedback error signal received by said function generator; and
   f. a second differential amplifier for subtracting the noise signal generated in said summing amplifier from the signal generated by said sensing means and amplifying the difference therebetween, thereby producing a filtered defect signal, said second differential amplifier having a first input port for receiving the signal from said sensing means, a second input port for receiving the noise signal from said summing amplifier and an output port at which the filtered defect signal is presented.

4. An apparatus as recited in claim 3 wherein said circuit means for producing the voltage signal indicative of the frequency and phase of said reoccurring noise comprises:
   a. a frequency detector for receiving the signal generated by said sensing means and for producing as an output signal a voltage indicative of the frequency of said reoccurring noise present in the received signal;
   b. a phase detector for determining the phase shift between the signal generated by said sensing means and the primary function signal generated by said function generator and for producing as an output signal a voltage representative of the phase shift, said phase detector having a first input port for receiving the signal generated by said sensing means, a second input port for receiving the primary function signal generated by said function generator, and an output port at which the voltage representative of the phase shift is presented; and
   c. a summing amplifier for receiving both the output signal of said frequency detector and the output signal of said phase detector and for producing as an output an amplified summation thereof, said output being the voltage signal indicative of the frequency and phase of said reoccurring noise present in the signal generated by said sensing means.

5. An apparatus for filtering an incoming signal to remove any reoccurring noise present in the incoming signal comprising:
   a. circuit means for receiving the incoming signal and for producing a voltage signal indicative of the frequency and phase of any reoccurring noise;
   b. a function generator for producing as its output a primary function signal synchronized in phase and frequency with said reoccuring noise present in the incoming signal, said primary function being a periodic sinusoidal wave, a first secondary function signal, said first secondary function signal being a square wave function, and a second secondary function signal, said second secondary function signal being a saw-tooth wave function, said function generator having a first input port for receiving a voltage signal indicative of the frequency and phase of said reoccuring noise, and a second input port for receiving a feedback error signal representing the differential existing between the noise signal produced by said function generator and the incoming signal;
   c. a summing amplifier having a first input port for receiving the primary function signal produced by said function generator, a second input port for receiving the first secondary function signal produced by said function generator, a third input port for receiving the second secondary function signal produced by said function generator, and an output port, said summing amplifier producing as an output a noise signal duplicative of any reoccuring noise present in the incoming signal, said noise signal being an amplified summation of the primary function signal, the first secondary function signal, and the second secondary function signal produced by said function generator;
   d. a first differential amplifier for subtracting the noise signal produced in said summing amplifier from the incoming signal, and for producing as an output signal an amplified reproduction of the differential therebetween, said output signal being the feedback error signal received by said function generator; and
   e. a second differential amplifier for substracting the noise signal generated in said summing amplifier from the incoming signal and for producing as an output an amplification of the difference therebetween, said differential amplifier having a first input port for receiving the incoming signal, a second input port for receiving the noise signal and an output port at which the amplification of the difference between the incoming signal and the noise signal is presented.

6. An apparatus as recited in claim 5 wherein said circuit means for producing the voltage signal indicative of the frequency and phase of said reoccurring noise comprises:
   a. a frequency detector for receiving the incoming signal and for producing as an output signal a voltage indicative of the frequency of said reoccurring noise present in the incoming signal;
   b. a phase detector for determining the phase shift between the incoming signal and the primary function signal generated by said function generator and for producing as an output signal a voltage representative of the phase shift, said phase detector having a first input port for receiving the incoming signal, a second input port for receiving the primary function signal generated by said function generator, and an output port at which the voltage representative of the phase shift is presented; and
   c. a summing amplifier for receiving both the output signal of said frequency detector and the output signal of said phase detector and for producing as an output an amplifier summation thereof, said output being the voltage signal indicative of the frequency and phase of said reoccurring noise present in the incoming signal.

* * * * *